US008778868B2

(12) United States Patent
van Gelder et al.

(10) Patent No.: US 8,778,868 B2
(45) Date of Patent: Jul. 15, 2014

(54) CHEMICALLY DEFINED VACCINE STABILISER

(75) Inventors: Petrus Theodorus Johannes Andries van Gelder, Boxmeer (NL); Arnoldus Theodorus Petrus Loermans, Boxmeer (NL); Mathias Arnold Maassen, Boxmeer (NL)

(73) Assignee: Intervet International B.V., Boxmeer (NL)

( * ) Notice: Subject to any disclaimer, the term of this patent is extended or adjusted under 35 U.S.C. 154(b) by 1340 days.

(21) Appl. No.: 11/908,028

(22) PCT Filed: Mar. 7, 2006

(86) PCT No.: PCT/EP2006/060507
§ 371 (c)(1),
(2), (4) Date: Sep. 3, 2009

(87) PCT Pub. No.: WO2006/094974
PCT Pub. Date: Sep. 14, 2006

(65) Prior Publication Data
US 2010/0028383 A1    Feb. 4, 2010

(30) Foreign Application Priority Data

Mar. 8, 2005 (EP) .................................. 05101774

(51) Int. Cl.
| | |
|---|---|
| *A61K 31/00* | (2006.01) |
| *A61K 31/04* | (2006.01) |
| *A61K 31/70* | (2006.01) |
| *A61K 31/132* | (2006.01) |
| *A61K 31/047* | (2006.01) |
| *A61K 31/7004* | (2006.01) |
| *A61K 31/7016* | (2006.01) |
| *A61K 31/198* | (2006.01) |
| *A61K 9/19* | (2006.01) |

(52) U.S. Cl.
CPC .............. *A61K 31/00* (2013.01); *A61K 31/132* (2013.01); *A61K 31/04* (2013.01); *A61K 31/047* (2013.01); *A61K 31/70* (2013.01); *A61K 31/7004* (2013.01); *A61K 31/7016* (2013.01); *A61K 31/198* (2013.01); *A61K 2300/00* (2013.01); *A61K 9/19* (2013.01)
USPC .................. 514/1; 514/23; 514/740

(58) Field of Classification Search
CPC ..... A61K 31/00; A61K 31/70; A61K 9/1623; A61K 9/4858; A61K 31/145; A61K 33/00; A61K 38/00; A61K 47/183; A61K 47/26; A61K 47/34; A61K 9/19
See application file for complete search history.

(56) References Cited

U.S. PATENT DOCUMENTS

| | | | | |
|---|---|---|---|---|
| 3,915,794 A | * | 10/1975 | Zygraich et al. ............ | 435/235.1 |
| 4,122,167 A | * | 10/1978 | Buynak et al. ............. | 424/211.1 |
| 4,374,201 A | | 2/1983 | Orlando et al. | |
| 4,500,512 A | | 2/1985 | Barme | |
| 4,710,378 A | | 12/1987 | Ohtomo et al. | |
| 5,618,539 A | | 4/1997 | Dorval et al. | |
| 6,231,860 B1 | | 5/2001 | Fanget et al. | |
| 6,565,888 B1 | * | 5/2003 | Tracy et al. ................... | 424/489 |
| 2003/0215455 A1 | * | 11/2003 | Reynolds et al. .......... | 424/184.1 |
| 2006/0148074 A1 | * | 7/2006 | Gorfien et al. ................ | 435/325 |

FOREIGN PATENT DOCUMENTS

| | | |
|---|---|---|
| CN | 1209067 | 2/1999 |
| EP | 0 392 717 A1 | 10/1990 |
| EP | 0 597 101 A1 | 5/1994 |
| WO | 9102543 | 3/1991 |
| WO | 9521860 | 8/1995 |
| WO | WO 97/23238 | 7/1997 |
| WO | 03029417 A2 | 4/2003 |
| WO | WO2004/039399 | 5/2004 |

OTHER PUBLICATIONS

Marten et al., Cytotechnology, 1999, 30:191-201.*
Taylor, Infection and Immunity, Sep. 1995, 63(9):3241-3244.*
Rizza et al., Trends in Immunology, 2002, 23(8):381383.*
Petrovsky et al., Immunology and Cell Biology, 2004, 82:488-496.*
Miles et al., Vaccine, 2005, 23:2530-2539.*
Makoschey, B. et al. (2002). Serum-free produced Bovine Herpesvirus type 1 and Bovine Parainfluenza type 3 virus vaccines are efficacious and safe. Cytotechnology, 39:139-145. Publisher Kluwer Academic, NL.
Bedu-Addo, Frank Kofi, Ph.D "Understanding Lyophilization Formulation Development", Pharmaceutical Technology, *Lyophilization*, pp. 10-18 (2004).
Carpenter, John F. et al. "Rational Design of Stable Lyophilized Protein Formulations: Some Practical Advice", Pharmaceutical Research, 14(8):969-975 (1997).
Da Costa, M.S. et al. "An Overview of the Role and Diversity of Compatible Solutes in *Bacteria* and *Archaea*", Advances in Biochemical Engineering/Biotechnology, 61:117-153 (1998).
Gatlin, Larry A. et al. "Protein Purification Process Engineering— Freeze Drying: A Practical Overview", Bioprocess Techn. 18:317-367 (1994).

(Continued)

*Primary Examiner* — Nicole Kinsey White

(57) ABSTRACT

The present invention relates to a stabilizer composition comprising an amino acid, and a sugar wherein all compounds are chemically defined; to a vaccine composition comprising such a stabilizer composition and a biological molecule and/ or a micro-organism; to a method for preparing a pharmaceutical composition comprising admixing such a stabilizer composition with a biological molecule and/or a micro-organism; to the use of such a stabilizer composition, and of vaccines prepared therewith.

4 Claims, No Drawings

(56) References Cited

OTHER PUBLICATIONS

Österberg, Thomas et al. "Development of a Freeze-Dried Albumin-Free Formulation of Recombinant Factor VIII SQ", Pharmaceutical Research, 14(7):892-898 (1997).

Pikal, Michael J. "Freeze-Drying of Proteins Part I: Process Design", BioPharm 3(8):18-27 (Sep. 1990).

Pikal, Michael J. "Freeze-Drying of Proteins Part II: Formulation Selection", BioPharm 3(9):26-30 (Oct. 1990).

* cited by examiner

CHEMICALLY DEFINED VACCINE STABILISER

CROSS REFERENCE TO RELATED APPLICATIONS

This application is a national phase filing under 35 U.S.C. §371 of International Application No. PCT/EP2006/060507, filed Mar. 7, 2006, which claims priority to European Patent Application No. EP 05101774.7, filed Mar. 8, 2005.

The present invention relates to a stabiliser composition comprising an amino acid, and a sugar wherein all compounds are chemically defined; to a vaccine composition comprising such a stabiliser composition and a biological molecule and/or a micro-organism; to a method for preparing a pharmaceutical composition comprising admixing such a stabiliser composition with a biological molecule and/or a micro-organism; to the use of such a stabiliser composition, and of vaccines prepared therewith.

In the bio-pharmaceutical industry involved in producing micro-organisms and biological molecules as products, the stability of these products is a major issue. Almost always, these products need to be formulated, stored and transported. Inevitably by influences experienced over time from temperature-changes and other physical or chemical influences, the materials produced lose their original effective quantity or desired qualitative properties. Consequently, conditions and additives for preventing such a loss of quality and/or of effective quantity are applied.

Much used stabilizing conditions are storage at reduced temperature, above or below zero ° C., and reduction of water content; especially useful is freeze-drying.

In freeze-drying a sample containing a biologically or pharmaceutically active molecule, a micro-organism, a cell, or a tissue is first frozen, and than dried under vacuum. Freeze-dried samples can then be stored at e.g. 4° C. and often remain stable for years. See for reviews: M. Pikal, 1990 (BioPharm, vol. 3, no. 8, p. 18-27 and no. 9, p. 26-30); L. Gatlin, et al., 1994 (Bioprocess Techn., vol. 18, p. 317-367); J. Carpenter et al., 1997 (Pharm. Research, vol. 14, p. 969-975); F. Bedu-Addo, 2004 (Pharm. Techn., 1 February, p. 10-18).

Ideally, a freeze-dried product has an almost unchanged quality and quantity of the freeze dried component(s) over a certain period of time, as well as a freeze-dried body or cake of attractive and elegant appearance, that can resist the physical influences of transportation, and that dissolves rapidly upon reconstitution in a diluent.

To achieve all these requirements for a freeze dried sample, and to make the sample 'survive' the various unfavourable conditions that occur during the freeze-drying process itself (freezing, drying, heating, cooling), the prolonged storage in freeze-dried state and the reconstitution, the sample to be freeze-dried is usually mixed with a stabilising composition prior to freeze-drying.

Compounds of a stabiliser composition are commonly termed: bulking agent, cake-former, lyoprotectant, tonicity modifier, surfactant, cryo(genic) protectant, freeze protectant, desiccant, lyophilisation agent, etc., wherein a specific compound can have several functions.

The term "compatible solute" is also used to indicate a compound that stabilizes molecules and organisms in conditions of a low water environment (M. S. da Costa et al. 1998, Adv. Bioch. Eng and Techn., vol. 61, p. 117-153).

Stabilising compositions, either for freeze-drying or for other stabilising uses, are complex mixtures of proteins, carbohydrates, lipids and salts; the composition of which can be adapted for each molecule or micro-organism to be stabilised, or for a specific purpose.

Although it is seldom known how a stabiliser functions exactly, the common finding is that large compounds of high molecular weight generally provide good stabilising effects. Therefore, of old the major ingredients used in stabilisers were such bulky compounds. To keep material-costs down they were taken from readily available products of animal origin, e.g.: milk powder, tryptose, gelatine, serum-albumin, collagen, casein hydrolysate, chondroitin sulphate, etc.

Unfortunately, the use of such compounds of animal origin potentially introduces the risk of contamination with extraneous agents of an otherwise sterile or controlled product. This has been a major concern ever since the discovery of intra-species zoonotic diseases and the newly discovered prion-related diseases. As a result, regulatory authorities have required extensive safety-testing of (stabilised) biological products for absence of extraneous agents before release onto the market.

This has led to abandonment of the use of such animal components, initially only in the culture media used in the production of the biological molecules or micro-organisms. For instance, B. Makoschey et al. (2002, Cytotechnology vol. 39, p. 139-145), describe a freeze-drying stabiliser for use in stabilising viruses that had been produced serum free; the stabiliser comprised sugars, amino acids, gelatin, and peptides from a hydrolysate of protein of animal origin.

Later, also the stabilisers that are used subsequently after production, were modified in their composition; as a result, stabiliser compositions were developed that are: serum free (without animal serum); protein free (without animal protein, but may contain other animal derived components) or even animal compound free (ACF) (not containing any component derived from an animal).

However, in the stabiliser compositions, the need remained for high molecular weight, large molecules for their stabilising effect. Therefore bulky compounds for ACF stabilisers were obtained for instance from plant or microbial origin, such as: yeastolate, soybean peptone, recombinant gelatine, (hydroxy-ethyl-) starch, alginate, etc.

Alternatively, large polymeric compounds of natural or synthetic origin are employed such as: polysaccharides, polyvinyl pyrrolidone, ficol, poly-lysine, poly-ethylene glycol, (carboxy-) methyl-cellulose, dextran, poly-sorbates (e.g. Tween® 80), etc. For instance T. Osterberg et al. (1997, Pharm. Res., vol. 14, p. 892-898), replaced serum albumin by Tween® 80 as stabilising compound for Factor VIII protein.

There are however several problems even with these ACF stabiliser compounds. For instance, several of these stabilising compounds are not resistant to heat sterilisation, and because sterility of the stabiliser composition is often an absolute requirement, the only other way to achieve this is then by the more tedious process of filter-sterilisation.

Also, in case the stabilised product is to be administered to a target human or animal, some of the ACF stabiliser compounds can not be used as they are toxic, or may cause allergic reactions.

Most prominent problem however in all these cases, is that the stabiliser-compositions, even when ACF, still share the common disadvantage that they contain or consist of unknown, heterogenous and ill-defined constituents. For instance the composition of the hydrolysates of natural vegetable products is not known at all. Similarly, for the polymer structures mentioned, their chemical structure is only known in general terms; the compounds used are only defined in that they have an average molecular size or an average length of the side chains. These molecules therefore actually comprise a family of chemical structures, with a wide variety of molecules.

Such compounds therefore still are of ill-defined nature, and have lot-to-lot variation. This requires careful selection of the starting compounds for suitable batches for production of a stabiliser composition. The batches of compounds that have the desired quality then have limited availability.

Use of such ill-defined compounds in stabilising compositions causes unknown and uncontrollable variations in composition, quality and yield of the products that are stabilised by these compositions.

Such an uncontrollable product quality is highly undesirable in an industry that is trying to produce consistent, safe, high quality products, and can only be overcome by costly and time-consuming procedures for selection of raw materials, verification of incoming goods, product release and final product quality control.

Object of the invention is to provide an alternative and improved stabiliser composition that does not suffer these disadvantages of the prior art.

Surprisingly it was found that a stabiliser composition comprising at least one amino acid, and at least one sugar, wherein all compounds are chemically defined, can provide efficient stabilisation of the quality and the quantity of biological molecules and of micro-organisms, without the need for high molecular weight, large, or ill-defined compounds. This provides many advantages over the prior art.

The stabilising composition of the invention is serum free, protein free and animal compound free, and therefore does not introduce any extraneous agents into the controlled product that is to be stabilised. Also the stabilising composition obviates the need for incorporation of ill-defined, heterogenous or unknown compounds, this results in product stabilisation leading to predictable and controllable end-products. Both aspects reduce the requirements for control on the end-products for quality and extraneous agents.

The stabilising composition comprises only exactly known compounds, not suffering from lot-to-lot variation, or limited availability of batches with required favourable characteristics. This reduces the requirements for the intake control and selection of starting materials. Further, the stabilising composition according to the present invention is non-toxic to target humans or animals, and is heat steriliseable.

The stabilising composition provides good stabilisation of biological molecules and of micro-organisms against physical and chemical influences, in particular it stabilises the quality and effective quantity of such samples against the negative influences experienced over time and through temperature-changes.

When used in freeze-drying, the stabilising composition stabilises biological molecules and micro-organisms against the process conditions of freezing, drying, heating, cooling, as well as against any negative influences during prolonged storage in freeze dried state and in reconstitution.

Also the stabilising composition provides a freeze-dried body or cake that is of attractive and elegant appearance, that can resist the physical influences of transportation, and that dissolves rapidly upon reconstitution in a diluent.

Therefore, the invention relates to a stabiliser composition comprising at least one amino acid and at least one sugar, characterised in that all compounds are chemically defined.

A "stabiliser composition" is defined as a composition that when admixed with biological molecules or micro-organisms has stabilising effect; i.e. the stabiliser composition can prevent to a large degree the loss of quality or effective quantity of samples containing biological molecules and/or micro-organisms.

The "effective quantity" is for instance the quantity of biologically or pharmaceutically active biological molecules, or the number of live or infectious micro-organisms.

The "loss of quality" might otherwise have occurred by physical and/or chemical influences, such as over time by variation in temperature, mechanical influences (e.g. transport) and/or changes in physical form (e.g. freezing, drying).

The stabiliser composition may be in the form of an aqueous solution, an aqueous concentrate, or may be provided as a dry mixture of chemicals suitable for preparing an aqueous solution or an aqueous concentrate of the stabiliser composition according to the invention.

The biological molecules and/or the micro-organisms that are to be stabilised can themselves be in liquid, dried, frozen, or freeze-dried form, before the admixing with the stabiliser composition.

The micro-organisms may be alive or dead, e.g. as result of deliberate inactivation.

A "sugar" is generally known to be a compound giving a sweet or sweetish taste, and more specifically is a carbohydrate such as a mono- or di-saccharide, a sugar-alcohol, or a polyol, and derivatives thereof.

For the invention, a compound is "chemically defined" when it consists exclusively of identical molecules.

Such a chemically defined compound therefore has a specifically known, unambiguous, and uniform chemical structure, and it is used in a specifically known quantity.

A chemically defined compound of the stabiliser according to the invention therefore is not an ill-defined, heterogenous or unknown compound such as a proteinaceous lysate, extract, hydrolysate, or peptide mixture. Also, no polymeric compound is comprised in the stabiliser composition according to the invention, of which only an average molecular weight, or an average length of the side chains is known.

A chemically defined compound of the stabiliser according to the invention is readily available from commercial suppliers of fine chemicals; preferably the highest purity available is employed. However, the requirement of being chemically defined does not rule out the presence of trace amounts of impurities in such a compound. Such impurities are for instance heavy metals, residues, solvents or the like. Preferably such impurities are present in an amount of less than 1% by weight of the chemically defined compound, more preferably less than 0.1, 0.01, 0.001, or 0.0001% by weight.

Preferably, the requirement of being chemically defined relates to the molecules of a compound of the stabiliser according to the invention, when in ionised form in an aqueous solution. Consequently, in a preferred embodiment such a chemically defined compound may in its solid or non-ionised form be present in different salt forms, or in forms having a different number of bound molecules of crystal water (hydrate forms).

Preferably the stabiliser composition according to the invention provides stabilisation of biological molecules and/or micro-organisms to at least the same level as prior art stabilisers comprising ill-defined compounds.

Preferably the loss of titre when using the stabiliser composition according to the invention for stabilisation of a product containing a live micro-organism, is less than 1 $Log_{10}$. More preferably less than 0.5 $Log_{10}$.

However this is not always required: for some applications, not having ill-defined compounds in the stabiliser and consequently in the final product is of overwhelming importance; a slightly lower yield in quality and/or quantity resulting from the use of the stabiliser composition according to the invention is in that case perfectly acceptable in exchange for the many advantages this offers over the prior art stabilisers.

This is for instance the case when the stabiliser according to the invention is to be used as stabiliser for long term storage of micro-organism seed material, such as in glycerol stocks. In that case ACF stabilisation by a fully defined stabiliser may be more important, and a loss in titre of up to 2 $\text{Log}_{10}$ may be acceptable, as such seed material will normally be cultured to the right quantity for inoculation of a new culture anyway.

Further, a skilled person is perfectly capable of further optimisations to for instance the composition of the stabiliser composition according to the invention, or the conditions for its use, by routine experimentation. Therefore, such optimised compositions and conditions are within the scope of the invention.

To assess the level of stabilisation, corresponding to the remaining effective quantity and quality of the stabilised product, any suitable technique can be used. For instance, the quantity and virulence (hence the quality) of viral and bacterial compounds can be quantified by titration or limiting dilution; biological molecules can be detected biochemically (e.g. enzymatically), immunologically (immuno-fluorescence test), or physically (e.g. electrophoresis, chromatography, or mass-spectrometry). All these techniques are well known and available in the art.

In a preferred embodiment, the stabiliser composition according to the invention additionally comprises at least one polyamine.

A "polyamine" is defined as a compound with two or more amino groups.

In more preferred embodiments, the invention relates to a stabiliser composition according to the invention:
  wherein the sugar is at least one selected from the group consisting of glucose, lactose, sucrose, maltose, trehalose, sorbitol and mannitol;
  wherein the polyamine is at least one selected from the group consisting of ethylene-diamine, cadaverine, putrescine, spermidine and spermine;
  wherein the amino acid is glutamate (glutamic acid) or glycine, or wherein both these amino acids are comprised.

In a further more preferred embodiment, the stabiliser composition according to the invention is a buffered aqueous solution; preferably the aqueous solution is buffered between pH 6-8, more preferably at about pH 6.9

The buffer can for instance be Tris/citrate, preferably at a concentration of about 50 mM/10 mM.

Preferably the buffer is phosphate based, more preferably di-sodium-phosphate di-hydrate.

Preferably the buffer is present in an amount of between 0.1 and 100 g/l, more preferably about 1 g/l.

In an alternate more preferred embodiment, the aqueous solution of the stabiliser composition according to the invention is a concentrated solution, comprising the compounds of the stabiliser composition in a concentration that is higher than the concentration at which these compounds will be in the final pharmaceutical composition that is formed upon admixing the stabiliser composition according to the invention with the biological molecules or the micro-organisms that are to be stabilised.

Preferably the stabiliser composition is 2×, 3×, 4×, 5×, 10, or 20× concentrated in comparison to the concentration or the amount in the final pharmaceutical composition; more preferably the stabiliser composition is 4× concentrated.

In a more preferred embodiment, a dry composition of chemicals is provided that is suitable for dissolving in an appropriate solvent, to prepare an aqueous solution or a concentrate of the stabiliser composition of the invention.

Providing a dry mixture of chemicals for later dissolution has the advantages of storage in a smaller volume. This saves storage space, and facilitates transportation and sales.

Even more preferably, in the stabiliser composition according to the invention:
  the sugar is sucrose, sorbitol, or mannitol; preferably sorbitol; more preferably D-sorbitol;
  the amino acid is glutamate or glycine; more preferably L-glutamate; even more preferably both L-glutamate and glycine are comprised;
  a combination of polyamines is used; more preferably spermine and putrescine, or spermine and ethylene diamine.

In a further more preferred embodiment of the stabiliser composition according to the invention, the 4× concentrate comprises:
  the sugar in an amount of between 10 and 200 g/l, preferably at about 75 g/l;
  the amino acid in an amount of between 0.1 and 400 g/l; preferably L-glutamate is comprised at about 20 g/l or glycine is comprised at about 160 g/l;
  the polyamine in an amount of between 0.1 and 100 g/l; preferably spermine is comprised at about 10 g/l or spermidine is comprised at about 2.5 g/l.

In a further preferred embodiment, the stabiliser composition according to the invention, comprises a sugar and glutamate as amino acid and additionally comprises at least one compatible solute. The compatible solute preferably is at least one selected from the group consisting of sarcosine, betaine, di-glycine, and choline. The compatible solute in the 4× concentrate is preferably present in an amount of between 0.1 and 400 g/l; preferably between 50-200 g/l, more preferably at about 160 g/l.

As outlined above, it is irrelevant in which form of salt or hydrate a compound of the stabiliser composition is used; for instance spermine can be used in the forms of: spermine, spermine-dyhydrate, or spermine tetra-hydrochloride; similarly, spermidine may be employed as spermidine, or spermidine tri-hydrochloride.

As the stabiliser according to the invention is intended to be admixed with biological molecules and/or micro-organisms, in some uses, the compounds of the stabiliser may be part of a product that is administered to a target human or animals. Therefore, the compounds of the stabiliser composition according to the invention preferably are non-toxic, at least: non-toxic in the concentrations present in the final product to be administered.

Preferably the compounds of the stabiliser composition according to the invention do not induce an unwanted allergic reaction.

Preferably, the stabiliser composition according to the invention is sterile. Sterilisation of the stabiliser according to the invention can be achieved by heat, filtration, irradiation or any suitable technique known in the art. Preferably the stabiliser composition is heat sterilised.

By way of non-limiting examples, chemically defined compounds suitable for use in the stabiliser composition according to the invention are listed in Table 1

TABLE 1

Chemically defined compounds suitable for use in the stabiliser composition according to the invention

| Product | Supplier | Catalogue nr. |
|---|---|---|
| Na$_2$HPO$_4$ di-hydrate | Merck | 6576 |
| D-Sorbitol | Sigma | S 7547 |
| Na-L-Glutamate mono-hydrate | Merck | 6445 |
| Glycine | Sigma | G 8790 |
| Spermine | Fluka | 85590 |
| Spermine tetra-hydrochloride | Fluka | 85610 |
| Spermine di-hydrate | Fluka | 85588 |
| Spermidine | Fluka | 85561 |
| Spermidine tri-hydrochloride | Fluka | 85580 |
| Putrescine | Sigma | P 7505 |
| Ethylene diamine | Aldrich | 19,580-4 |
| Tris-HCl (Trishydroxymethyl-aminomethane) | Merck | 8382 |
| tri-Na Citrate di-hydrate | Merck | 6447 |
| Sarcosine | Sigma | S 7672 |
| Betaine | Sigma | B 7045 |
| Di-glycine | Sigma | G 3915 |
| Choline | Sigma | C 2004 |

As is known in the art, derivatives of the herein described compounds of the stabiliser composition according to the invention, are available, or can be synthesised. Such derivatives are also suitable for use as compounds of the stabiliser composition according to the invention. Therefore, such derivatives are within the scope of the invention.

TABLE 2

Overview of the preferred and most preferred stabiliser compositions according to the invention. Amounts given correspond to those of a 4x concentrate:

| | | Amount in g/l in a 4 × concentrate | |
|---|---|---|---|
| | | Preferred | Most preferred |
| Buffer | | 0.1-100 | |
| | Na$_2$HPO4 | idem | 1 |
| | or Tris/Citrate | id. | 50 mM/10 mM |
| Sugar | | 10-200 | |
| | Sorbitol | id. | 75 |
| Amino-acid | | 0.1-400 | |
| | Glutamate | id. | 20 |
| | and/or Glycine | id. | 160 |
| Polyamine | | 0.1-100 | |
| | Spermine | id. | 10 |
| | or Spermidine | id. | 2.5 |
| | or Putrescine | id. | 10 |
| | or Ethylene-diamine | id. | 10 |
| | or combinations: | | |
| | spermine | | 10 |
| | and putrescine | | 5 |
| | or | | |
| | spermine | | 10 |
| | and ethylene diamine | | 5 |
| Compatible solute | | 0.1-400 | |
| | Sarcosine | id. | 160 |
| | or Betaine | id. | 160 |
| | or Di-glycine | id. | 160 |
| | or Choline | id. | 160 |
| pH | | 6-8 | 6.9 |

A large number of experiments were performed with stabiliser compositions according to the invention. These were designed to incorporate all conditions under which the stabiliser composition according to the invention provides effective stabilisation:

cooling; for storage of (bulk) product in liquid form at e.g. 4° C.

freezing; for storage of (bulk) product deep frozen, at e.g. −20° C., or −45° C.

freeze-drying; incorporating: drying, heating, cooling freezing of freeze-dried product; for storage deep frozen, at e.g. −20° C., or −45° C.

cooling of freeze-dried product; for storage at 4° C.

heating of freeze-dried product, to temperatures above room temperature, and reconstitution of freeze-dried product in a diluent.

When these experiments were performed with stabilised compositions comprising micro-organisms, the remaining number of live infective micro-organisms in the reconstituted products were determined using well known quantification techniques based on titration or limiting dilution. When performed with biological molecules, the quality and quantity was determined using specific assays such as titration, Elisa, or bio-assays.

These experiments and their results are summarised in the examples, and show that the stabiliser composition according to the invention provides for efficient stabilisation of micro-organisms and or biological molecules, not only for the various uses in and around freeze-drying, but also to stabilisation of bulk antigen in cooled or in frozen storage, prior to or in stead of freeze-drying.

In an alternate embodiment, the stabiliser composition of the invention is characterised in that no compounds of high molecular weight or large size are comprised.

For the invention, "high molecular weight" and "large" compounds, are defined as any compound having a molecular weight or size of the molecular ion that exceeds 203 Da. For instance, spermine would not be such a large compound, as its molecular ion has a molecular weight of only 202 Da, when excluding any crystal water, or salt-forms, such as hydrates, or (hydro) chlorides.

As described above, it was surprising to find none of the bulky compounds commonly used in the art are required to achieve efficient stabilisation, in fact no compound larger than spermine is required.

The advantages of this have also been mentioned; the high-molecular weight, large compounds often are ill-defined and heterogenous, or at best are compounds of which only an average molecular size or an average length of the side chains is known. Consequently, such ill-defined compounds used in a stabiliser composition will result in a stabilised product with unpredictable characteristics.

In an alternate preferred embodiment, the invention relates to a vaccine composition comprising a stabiliser composition according to the invention, and at least one biological molecule or at least one micro-organism, or a combination thereof.

A vaccine composition is commonly known in the art to represent a composition comprising an immunogenic compound in a pharmaceutically acceptable carrier, which immunogenic compound is capable of inducing a passive or active activation of a targets' immune system. The induced immune response is meant to interfere which the establishment or the progression of a certain infection, or to ameliorate symptoms of disease.

A pharmaceutically acceptable carrier can be e.g. sterile water or a sterile physiological salt solution. In a more complex form the carrier can e.g. be a buffer.

A "biological molecule" for the invention is understood to be a molecule that can be found in nature; in particular this refers to a protein, carbohydrate, lipid, or nucleic acid. The origin of the molecule may be biologic or synthetic, derived either ex vivo or ex vitro.

The term "protein" is meant to incorporate a molecular chain of two or more amino acids; therefore peptides, oligopeptides and polypeptides are included within the definition of protein.

The vaccine composition according to the invention may be in any form, e.g.: freeze-dried, liquid, or frozen; or may be formulated or processed to a liquid, a gel, an ointment, a powder, a tablet, a capsule, or a freeze-dried body depending on the desired method of storage, transportation or application to the target.

The vaccine composition according to the invention may comprise single immunogenic micro-organisms and biological molecules or combinations thereof.

In preferred embodiments, the invention relates to a vaccine composition:
wherein the micro-organism is a virus or a bacterium, or wherein both a virus and a bacterium are comprised; more preferably the virus is at least one viral species selected from the group consisting of herpes-, paramyxo-, orthomyxo-, adeno-, rhabdo-, birna-, corona-, pneumo-, and poxvirus; even more preferably the virus is selected from the group consisting of Bovine herpes virus, bovine parainfluenzavirus 3, pseudorabies virus, human respiratory syncytial virus, and human or animal influenza virus; more preferably, the bacterium is selected from the group consisting of the bacterial species *Streptococcus, Staphylococcus, Escherichia, Mycoplasma, Edwardsiella, Campylobacter* and *Salmonella*.
wherein the biological molecule is at least one selected from the group consisting of a protein, a carbohydrate, a lipid, and a nucleic acid; more preferably the protein is at least one selected from the group consisting of an antibody, an antibody-fragment, a cytokine, a hormone, and an enzyme.

Antibody fragments are e.g. Fab fragments and single chain antibodies. Hormones for use with the stabiliser composition of the invention are for example insulin, gonadotrophic hormones such as follicle stimulating hormone, human chorion gonadotrophin and erythropoietin.

The vaccines and stabiliser compositions of the invention are applicable with a wide variety of viruses, of any genomic or morphologic type, infective to any species of animal, or to humans. In particular, any results presented on stabilisation of a particular animal virus can be extrapolated directly to predict the results of stabilisation of the corresponding virus infecting an other host species, either animal or human, and to the other viral species within its viral family.

Viruses having a viral envelope are particularly sensitive to chemical and physical influences. Consequently, as such viruses can be effectively stabilised by the stabiliser composition of the invention, this proves its efficacy even more.

TABLE 3

Examples of viruses for use with the stabiliser composition of the invention

| family | example | genome | enveloped |
|---|---|---|---|
| herpes | bovine herpes virus (BHV)* | ds DNA | yes |
| id. | pseudorabies virus (PRV) | id. | yes |
| pox | myxomavirus | id. | yes |
| paramyxo | bovine parainfluenzavirus 3 (PI3) | ss RNA, negative strand | yes |
| pneumo | bovine respiratory syncytial virus (BRSV) | id. | yes |
| orthomyxo | equine influenza virus (EIV) | id., segmented | yes |
| corona | bovine coronavirus (BCV) | ss RNA, positive stranded | yes |

*Bovine herpes virus is also known as infectious bovine rhinotracheitis virus

The bacteria for use with the stabiliser according to the invention can be of any type, for instance as characterised by staining Gram positive or Gram negative.

TABLE 4

Examples of bacteria for use with the stabiliser composition of the invention:

| characteristic | name |
|---|---|
| Gram positive | *Streptococcus equi* |
| id. | *Staphylococcus carnosus* |
| Gram negative | *Escherichia coli* |
| id | *Edwardsiella ictaluri* |
| id. | *Salmonella gallinarum* |

Results obtained in stabilising these bacteria can be extrapolated to other bacterial species within the genuses mentioned.

The production system used for producing biological molecules and micro-organisms for use with the stabiliser of the invention can be any in vitro or an in vivo system. For instance viruses can be produced in a cell culture, on fertilized chicken eggs, or in a host animal; bacteria can be produced using similar techniques, and additionally in culture broth, and biological molecules can be produced by isolation from an animal or micro-organism, especially recombinant expression systems can be used advantageously. Many other embodiments are known in the art.

However, the optimal safety and predictability of the stabilised end-product is achieved by removing unknown, heterogenous and ill-defined constituents from both the production stage and the stabiliser composition.

Therefore, in a more preferred embodiment of the vaccine composition according to the invention, the biological molecule or the micro-organism, or both, were produced animal-component free.

ACF production systems for instance are viral cultures on cells in ACF media; bacterial cultures in an ACF culture broth; and recombinant expression cultures using ACF media, e.g. the baculovirus expression system using insect cells.

In a further preferred embodiment, the vaccine composition according to the invention additionally comprises an adjuvant.

Adjuvants are commonly used to boost the immune response to a vaccine component, by stimulating the immune system of a target human or animal, in a non-specific manner. Many different adjuvants are known in the art, for example: mineral or biological oils, saponins, peptides, alumina and derivatives, etc.

In a further preferred embodiment, the vaccine composition according to the invention is freeze-dried.

In freeze-dried form the stabiliser composition of the invention will be most benificiary; the freeze-dried vaccine compositions according to the invention are stable at for instance +4° C. for months to several years.

Procedures for freeze-drying are known in the art; equipment for freeze-drying at different scales is available commercially. Typically vaccine compositions comprising a stabiliser according to the invention are filled in containers such as glass vials to a certain volume, e.g. between 0.5 and 50 ml, preferably 1, 2, or 5 ml. Subsequently these vials are frozen, and submitted to a freeze-drying process.

An outline of an exemplary freeze-drying process comprises the steps of:

deep freezing for 10-60 minutes, to fix the liquid into a certain structure;

first drying step at −20 to 20° C., for 1-12 hours, at high vacuum, to sublimate the crystallised water;

secondary drying at 0 to 40° C., for 12-6 hours, at medium vacuum, to desorb the unfrozen water;

packing the freeze dried bodies (e.g. closing glass vials by a rubber stopper) to maintain dry conditions, e.g under vacuum, or under nitrogen gas; and hold on +4° C.

The skilled person is very well capable of routine variations and optimisations to such a process in order to achieve the best results for a specific type of sample.

The freeze-drying process can be optimised by monitoring the temperature, and the water content in the apparatus during drying. Also, differential scanning calorimetry is routinely used to assess the characteristics of the product before and after freeze-drying.

Residual water content (rwc) in the end product is an important parameter determining the freeze-dried products' stability. Preferably the rwc of freeze-dried samples and vaccines according to the invention is below 5%. To determine the rwc, Karl Fischer titration known in the art can advantageously be employed.

In a further preferred embodiment, a freeze-dried vaccine according to the invention is prepared in the form of a lyosphere as described in European patent EP 799.613.

The freeze-dried body produced of a vaccine composition according to the invention can be in any form. The stabilising composition according to the invention provides beneficiary characteristics to the vaccine composition to achieve an elegant and attractive appearance of the freeze-dried body. Preferably the freeze-dried cake in a glass vial is of shiny, homogenous appearance, and preferably stays attached to the wall of the vial upon flicking it, and is not so brittle that it becomes pulverised under normal transportation conditions.

Consequently, the desired appearance of the freeze-dried vaccine body not only relates to subjective or aesthetic characteristics, but also comprises genuine advantageous technical effects; in particular the stabilisation efficacy, the resistance to the rigours of transportation, and the redissolution speed are involved.

Of special interest is to avoid an appearance known in the art as "collapsed", as freeze-dried bodies having such an amorphous and clumped appearance redissolve slowly and incompletely, and do not provide adequate stabilisation of the biological molecules and/or micro-organisms that are to be conserved.

In a further preferred embodiment, a ready for use vaccine solution is obtainable by reconstituting a freeze-dried vaccine composition according to the invention in a pharmaceutically acceptable carrier.

As the freeze-dried vaccine compositions according to the invention dissolve rapidly, preferably the reconstitution is performed immediately before the vaccine solution is to be applied to a target. This ascertains the vaccine solution is fresh and of the intended dose and quality.

The vaccine composition according to the invention can be administered to a human or animal target according to methods known in the art. For instance by parenteral applications such as through all routes of injection into or through the skin: e.g. intramuscular, intravenous, intraperitoneal, intradermal, sub mucosal, or subcutaneous. Alternative routes of application that are feasible are by topical application as a drop, spray, gel or ointment to the mucosal epithelium of the eye, nose, mouth, anus, or vagina, or onto the epidermis of the outer skin at any part of the body; by spray as aerosol, or powder. Alternatively, application can be via the alimentary route, by combining with the food, feed or drinking water e.g. as a powder, a liquid, or tablet, or by administration directly into the mouth as a liquid, a gel, a tablet, or a capsule, or to the anus as a suppository. Also immersion vaccination can be applied advantageously.

The preferred application routes are intramuscular or subcutaneous injection, or intranasal spray.

It goes without saying that the optimal route of application will depend on the specific particularities of the infection or symptoms that are to be prevented or ameliorated, the characteristics of the vaccine formulation that is used, and the particular characteristics of the target species.

The scheme of the application of the vaccine composition according to the invention to the target human or animal can be in single or multiple doses, which may be given at the same time or sequentially, in a manner compatible with the dosage and formulation, and in such an amount as will be immunologically effective, for instance as a single yearly dose.

In an alternate embodiment, the invention relates to a method for preparing a pharmaceutical composition, comprising admixing a stabiliser composition according to the invention with a composition comprising at least one biological molecule or at least one micro-organism, or a combination thereof.

The pharmaceutical composition prepared according to the method of the invention can be in any form: liquid or dry, frozen, freeze-dried, etc.

The admixing can be performed using any suitable technique available in the art.

Preferably the method according to the invention comprises admixing 1 part of the stabiliser composition according to the invention as a sterile aqueous buffered solution at 4× concentration, with 3 parts of a composition comprising at least one biological molecule and/or at least one micro-organism, to produce a pharmaceutical composition according to the invention.

The composition comprising at least one biological molecule or at least one micro-organism, or a combination thereof, that is to be admixed with the stabiliser composition according to the invention, is preferably in liquid form. This composition can be obtained from a viral or bacterial culture, or an expression system culture. This composition can for instance be obtained after downstream-processing, such as centrifugation, e.g. the culture supernatant, or the (resuspended) centrifuged pellet (comprising virus-infected cells or bacteria); or the unprocessed whole culture may be used.

Preferably the admixing of stabiliser composition and composition comprising a biological molecule and/or a micro-organism according to the method of the invention, is performed shortly after production and down-stream-processing have finished, in order to achieve the best stabilisation results.

Preferably the stabilised pharmaceutical composition thus obtained is than stored cooled or frozen, awaiting further processing and the results of quality control on the production harvest.

In preferred embodiments of the method according to the invention:

the micro-organism is a virus or a bacterium, or both a virus and a bacterium are comprised.

the virus is at least one viral species selected from the group consisting of herpes-, paramyxo-, orthomyxo-, adeno-, rhabdo-, birna-, corona-, pneumo-, and poxvirus.

the biological molecule is at least one selected from the group consisting of a protein, a carbohydrate, a lipid, and a nucleic acid.

the protein is at least one selected from the group consisting of an antibody, an antibody-fragment, a cytokine, a hormone, and an enzyme.

the biological molecule or the micro-organism, or both, were produced animal-component free.

the resulting pharmaceutical composition is subjected to freeze-drying.

In a more preferred embodiment, the invention relates to a pharmaceutical composition obtainable by the method according to the invention, wherein the composition is a vaccine.

In an even more preferred embodiment, the invention relates to a method of preparing a vaccine solution by reconstituting a pharmaceutical composition according to the invention, in a pharmaceutically acceptable carrier.

In a further alternate embodiment, the invention relates to the use of a stabiliser composition according to the invention for stabilising the quality and/or the quantity of at least one biological molecule or at least one micro-organism, or a combination thereof, in a composition.

In preferred embodiments of the use according to the invention:

the micro-organism is a virus or a bacterium, or both a virus and a bacterium are comprised.

the virus is at least one viral species selected from the group consisting of herpes-, paramyxo-, orthomyxo-, adeno-, rhabdo-, birna-, corona-, pneumo-, and poxvirus.

the biological molecule is at least one selected from the group consisting of a protein, a carbohydrate, a lipid, and a nucleic acid.

the protein is at least one selected from the group consisting of an antibody, an antibody-fragment, a cytokine, a hormone, and an enzyme.

the biological molecule or the micro-organism, or both, were produced animal-component free.

In a more preferred embodiment, the invention relates to the use according to the invention, of a vaccine solution according to the invention, or a vaccine solution obtainable by the method of the invention, for immunisation of a target human or animal.

The invention will now be further described with reference to the following, non-limiting, examples.

EXAMPLES

As mentioned above, freeze-drying experiments were performed incorporating all conditions under which an effective stabiliser must be able to stabilise: cooling, freezing, drying, heating.

The general outline of the freeze-drying experiments performed in stabilising micro-organisms was as follows:

compositions comprising micro-organisms were obtained from a culture, processed if required and stored at 4° C. or below zero ° C.

a stabiliser composition according to the invention was prepared by weighing the required compounds in the desired quantities, adding these to a required volume of sterile distilled water, and mixing until dissolved. The stabiliser composition was then heat sterilised at 121° C. for 20 minutes.

at start of the experiment the sample was thawed, mixed with a volume of a 4× concentrated stabiliser that was one third of the sample volume. Either the stabiliser according to the invention, or reference stabiliser compositions were used. Also samples without any stabiliser were comprised in the experiments.

stabilised samples were put into standard 10 ml glass vials at a certain filling volume: BHV, and PI3 virus at 2 ml, and PRV, myxoma virus, BRSV, EIV and BCV at 1 ml. Bacterial samples were filled at 2.5 ml per vial.

samples were freeze-dried using a standard two-stage program, to a residual water content below 5%, and then sealed under vacuum with a rubber stopper.

subsequently samples were stored at 4° C. or at higher temperatures for a certain period of time; results in the columns "direct 4° C." are results of titrations on samples stored at 4° C. for less than 1 month after freeze-drying; results in columns "3 days 28° C." are titration results of samples stored at 28° C. for 3 days subsequently to possible storage at 4° C. after freeze-drying, and then quantified immediately after these three days; results in columns "1 year 4° C." are titration results of samples stored at 4° C. for at least one year after freeze-drying.

Storage at 28° C. for three days is incorporated as an accelerated stability assay; most times these results are indicative for the consequences of storage over longer time at ambient or cooled conditions.

In order to determine the amount and the quality of the micro-organism that remained after these treatment conditions, virus samples were infectivity-titrated, and bacterial samples were plate-counted.

BRSV Titration Assay:

Stabilised samples of BRS virus was diluted in standard cell culture medium supplemented with FCS 10% (v/v), to dilutions between $10^{-1}$ and $10^{-7}$, in 0.2 ml. The dilutions are inoculated on BEL cells in the wells of a micro titre plate: $1.5\times10^5$ BEL cells/ml, at 0.2 ml/well. 10 wells were used per viral dilution. The micro titre plates are incubated during 8 days (3-5% $CO_2$, 37° C.). The plates are fixed using Acetone/PBS 70/30% v/v, during 10-15 minutes at room temperature. The fixed monolayer is incubated initially with a monoclonal antibody specific for BRSV and secondary with an anti-antibody FITC-conjugate+Evans blue (as counter stain). Those dishes in which positive fluorescent cells have developed are scored as positive. Virus titres are calculated according to Reed and Muench, and expressed as viral titre in $TCID_{50}$.

In all experiments a homologues standard virus sample and negative control was included for every run of virus titrations. All virus titrations were carried out in duplo on one day. The averaged titres are presented.

Myxoma Virus Titration Assay:

RK13 cells are seeded in 96 well plates, at $4\times10^5$ cells per ml, at 100 µl per well, in standard cell-culture medium with 5% foetal calf serum (FCS) and appropriate antibiotics. The plates are incubated overnight at 37° C., in 5% $CO_2$ atmosphere.

Next day a stabilised sample containing myxomavirus is diluted from $10^{-1}$ through $10^{-8}$. 20 µl of each viral dilution is inoculated onto a well of the RK13 cell plate, in triplicate. After an incubation of an hour at 37° C./5% $CO_2$, 100 µl of fresh culture medium with FCS is added to the wells, and the plates are incubated for another 2-3 days, until viral plaques are clearly visible, and CPE can be read.

Plates are then emptied, stained with a dilution of Naphtalene black, incubated for 1 hour at room temperature. The plates are emptied again, washed with tap water, dried, and read using light microscopy.

The number of live infective myxoma viruses in the original sample is calculated by Spearman-Kärber algorithm, and expressed as a $TCID_{50}$ value.

BHV, PI3, and PRV Virus Titration Assay:

Stabilised samples of BHV, PI3, and PRV virus were titrated in a manner similar to that for myxoma virus, except that for BHV and PI3 virusses JCK cells, and for PRV Vero cells were used. CPE was also determined by counting plaques using light microscopy.

BCV Titration Assay:

A cell suspension of MDBK cells is plated in 96 well plates, at 200 µl/well of $1 \times 10^5$ cells/ml in DMEM medium with 10% FCS and appropriate antibiotics. Plates are incubated for 3 days at 37° C. in 5% $CO_2$ atmosphere. After three days a confluent monolayer has formed. Medium is removed, fresh 200 µl medium without FCS is added, and plates are incubated for 2 hours. Dilutions of BCV from stabilised samples are prepared in steps of 10 fold dilutions. The microtiter plates are emptied again, and dilutions between $10^{-3}$ and $10^{-8}$ are inoculated on the MDBK cell-monolayer. Plates are incubated for 5-6 days. Viral plaques are visualised for immunofluoresecnce counting, using a polyclonal rabbit anti BCV serum, and a Goat-anti-rabbit-FITC labeled conjugated antibody. After counterstaining with Evans blue, plaques are counted using UV-light microscopy. Calculation of live viral $TCID_{50}$ titre in the stabilised sample is by Reed-Muench algorithm.

Equine Influenza Virus

EIV is titrated on chicken eggs; dilutions of a stabilised EIV sample are inoculated into the allantoic cavity of a fertilized live 10 day old chicken egg, and incubated at 40-42° C. for 3-5 days. Eggs are opened, and a sample of allantoic fluid is tested in heamagglutination assay using chicken red blood cells. The amount of live infectious EIV in the original sample is calculated from the highest dilution giving a HA reaction.

In some experiments the quality of the freeze-dried cake was judged. This comprised visual inspection and shaking of the vial.

An arbitrary indication was given:

+ elegant appearance, good firm structure 0 adequate appearance and structure

− less than desired appearance and structure

Bacteria

Bacterial cultures were obtained by growing stock material in shaker flasks in appropriate standard growth media. Next, these cultures were quantified, by plating out in duplo a series of limiting dilution samples on blood-agar plates, for counting the number of colonies appearing after overnight incubation. For some experiments the number of colonies recovered after freeze drying were expressed as % of the number of colonies in the original culture before freeze drying.

The corresponding cultures were then mixed 1:4 with a 4× concentrated stabiliser composition according to the invention, and submitted to a standard two-stage freeze drying program.

For the experiments involving *E. coli*, a K12 strain was used, and different culture media were used: standard LB medium, LB with ampicillin, and blood-agar medium. The efficacy of the stabiliser composition according to the invention was compared to that of a standard stabiliser containing albumin.

Samples were tested either before or directly after freeze-drying, or after 3 days of incubation at 28 or 30° C., again by way of accelerated stability assay.

TABLE 5

Effect of concentration of Glycine
Micro-organism used: BHV
Stabiliser composition used:

| | Compound | g/l (4x conc) |
|---|---|---|
| Buffer | $Na_2HPO_4$ di-hydrate | 1 |
| Sugar | D-Sorbitol | 75 |
| Amino-acid | Na-L-Glutamate mono-hydrate | 20 |
| | and Glycine | variable |
| Polyamine | Spermine tetra-hydrochloride | 10 |

| Exp. code 03AL | Wet titre before | Virus titre ($log_{10}$ $TCID_{50}$/vial) Titre after freeze drying | | | |
|---|---|---|---|---|---|
| Glycine g/l | freeze-drying | Direct | 3 days 28° C. | 1 year 4° C. | Cake quality |
| 240 | 9.0 | 8.2 | 7.9 | 7.9 | 0 |
| 200 | | 8.4 | 8.1 | 7.9 | 0 |
| 160 | | 8.2 | 8.1 | 8.2 | + |
| 120 | | 8.4 | 8.1 | 8.2 | 0 |
| 80 | | 8.4 | 8.3 | 8.3 | − |
| 40 | | 8.5 | 7.9 | 7.8 | − |
| 0 | | 8.0 | 7.7 | 7.9 | − |

TABLE 6

Effect of concentration of Glutamate
Micro-organism used: BHV
Stabiliser composition used:

| | Compound | g/l (4x conc) |
|---|---|---|
| Buffer | $Na_2HPO_4$ di-hydrate | 1 |
| Sugar | D-Sorbitol | 75 |
| Amino-acid | Na-L-Glutamate mono-hydrate | variable |
| | and Glycine | 160 |
| Polyamine | Spermine tetra-hydrochloride | 10 |

| Exp. code 03AL | Wet titre before | Virus titre ($log_{10}$ $TCID_{50}$/vial) Titre after freeze drying | | | |
|---|---|---|---|---|---|
| Glutamate g/l | freeze-drying | Direct | 3 days 28° C. | 1 year 4° C. | Cake quality |
| 0 | 9.0 | 8.2 | 7.9 | 8.4 | 0 |
| 20 | | 8.4 | 8.1 | 7.7 | + |
| 100 | | 8.2 | 8.1 | 7.9 | − |

TABLE 7

Type of polyamine and effect of concentration of polyamine
Micro-organism used: BHV
Stabiliser composition used:

| | Compound | g/l (4x conc) |
|---|---|---|
| Buffer | $Na_2HPO_4$ di-hydrate | 1 |
| Sugar | D-Sorbitol | 75 |
| Amino-acid | Na-L-Glutamate mono-hydrate | 20 |
| | and Glycine | 160 |
| Polyamine | Spermine tetra-hydrochloride | variable |
| | or Spermidine tri-hydrochloride | variable |

| Exp. code 03AL | Wet titre before | Virus titre ($log_{10}$ $TCID_{50}$/vial) Titre after freeze drying | | | |
|---|---|---|---|---|---|
| Spermine g/l | freeze-drying | Direct | 3 days 28° C. | 1 year 4° C. | Cake quality |

TABLE 7-continued

Type of polyamine and effect of concentration of polyamine
Micro-organism used: BHV
Stabiliser composition used:

|   |   |   |   |   |   |
|---|---|---|---|---|---|
| 0 | 9.0 | 8.0 | 7.8 | n.a. | + |
| 0.5 |  | 8.3 | 7.8 | 8.0 | 0 |
| 2.5 |  | 8.2 | 8.0 | 8.2 | + |
| 10 |  | 8.2 | 8.1 | 8.2 | + |
| 30 |  | 8.3 | 8.0 | 8.5 | + |
| 50 |  | 8.1 | 8.2 | 7.9 | 0 |

| Spermidine g/l | before freeze-dr. | Direct | 3 days 28° C. | 1 year 4° C. | Cake quality |
|---|---|---|---|---|---|
| 0.5 | 9.0 | 8.7 | 8.1 | 7.5 | 0 |
| 2.5 |  | 8.5 | 8.1 | 8.1 | 0 |
| 10 |  | 8.4 | 7.8 | 8.4 | 0 |
| 30 |  | 8.2 | 8.0 | 7.9 | − |
| 50 |  | n.a. | n.a. | 8.1 | n.a. |

|  | before freeze-dr. | Direct | 3 days 28° C. | 1 year 4° C. | Cake quality |
|---|---|---|---|---|---|
| Conv. stab | 9.0 | 8.2 | 8.0 | 7.9 | + |

NB: in these experiments either Spermine or Spermidine was comprised in the stabiliser composition.
For reference purposes, a prior art conventional stabiliser (Makoschey et al., supra) was included as comparative example, this is indicated as "Conv. stab."
n.a. = not available

TABLE 8

Type of polyamine-salts and hydrates and effect of concentration

Micro-organism used: BHV
Stabiliser composition used:

| | Compound | g/l (4 × conc) |
|---|---|---|
| Buffer | Na$_2$HPO$_4$ di-hydrate | 1 |
| Sugar | D-Sorbitol | 75 |
| Amino-acid | Na-L-Glutamate mono-hydrate | 20 |
|  | and Glycine | 160 |
| Polyamine | Spermine tetra-hydrochloride | variable |
|  | or Spermine di-hydrate | variable |
|  | or Putrescine* | variable |
|  | or Ethylene diamine* | variable |

*in these experiments either one polyamine was comprised or a combination; this is indicated in the table
Exp. code 03AA

| Spermine tetra-hydrchl. g/l | Wet titre before freeze-drying | Virus titre (log$_{10}$ TCID$_{50}$/vial) Titre after freeze drying | | |
|---|---|---|---|---|
| | | Direct | 3 days 28° C. | 1 year 4° C. |
| 10 | n.a. | 8.2 | 8.1 | 7.9 |
| 30 |  | 7.8 | 7.5 | 7.5 | n.a. = not available

Exp. code 03AB

| Spermine dihydrate g/l | Wet titre before freeze-drying | Virus titre (log$_{10}$ TCID$_{50}$/vial) Titre after freeze drying | | |
|---|---|---|---|---|
| | | Direct | 3 days 28° C. | 1 year +4° C. |
| 5 | 9.1 | 7.8 | 6.9 | 7.3 |
| 10 |  | 7.4 | 6.7 | 7.4 |
| 30 |  | 7.5 | 6.6 | 7.1 |

| Spermine tetra-hydrchl. g/l | before freeze-dr. | Direct | 3 days 28° C. | 1 year +4° C. |
|---|---|---|---|---|
| 5 | 9.1 | 8.1 | 7.5 | 7.6 |
| 10 |  | 8.0 | 7.7 | 7.8 |
| 30 |  | 7.7 | 7.0 | 7.4 |

Exp. code 03AJ

| Spermine tetra-hydrchl. g/l | Wet titre before freeze-drying | Virus titre (log$_{10}$ TCID$_{50}$/vial) Titre after freeze drying | | |
|---|---|---|---|---|
| | | Direct | 3 days 28° C. | 1 year +4° C. |
| 10 | 8.5 | 8.5 | 7.9 | 7.8 |

| Putrescine g/l | before freeze-dr. | Direct | 3 days 28° C. | 1 year +4° C. |
|---|---|---|---|---|
| 5 | 8.5 | 8.0 | 7.5 | 7.3 |
| 10 |  | 8.1 | 7.6 | 7.9 |
| 30 |  | 8.0 | 7.5 | 7.7 |

| Ethylenediamine g/l | before freeze-dr. | Direct | 3 days 28° C. | 1 year +4° C. |
|---|---|---|---|---|
| 5 | 8.5 | 8.0 | 8.0 | 7.7 |
| 10 |  | 8.2 | 7.8 | 7.9 |
| 30 |  | 8.2 | 7.4 | 8.2 |

| no polyam. | before freeze-dr. | Direct | 3 days 28° C. | 1 year +4° C. |
|---|---|---|---|---|
| 0 | 8.5 | 8.1 | 7.3 | 7.4 |

| Combined polyamines* | before freeze-dr. | Direct | 3 days 28° C. | 1 year +4° C. |
|---|---|---|---|---|
| A | 8.5 | 8.4 | 7.8 | 8.2 |
| B |  | 8.5 | 8.2 | 8.2 |

*Polyamine combinations:
A = Spermine tetra-hydrochloride 10 g/l, and Putrescine 5 g/l.
B = Spermine tetra-hydrochloride 10 g/l, and Ethylene diamine 5 g/l.

TABLE 9

Stabilisation of different viruses, and effect of polyamine
Stabiliser compositions used:

| | Compound | g/l (4x conc) |
|---|---|---|
| | "invention 1" | |
| Buffer | Na$_2$HPO$_4$ di-hydrate | 1 |
| Sugar | D-Sorbitol | 75 |
| Amino-acid | Na-L-Glutamate mono-hydrate | 20 |
|  | and Glycine | 160 |
| Polyamine | Spermine tetra-hydrochloride | 10 |
| | "invention 2" | |
| Buffer | Na$_2$HPO$_4$ di-hydrate | 1 |
| Sugar | D-Sorbitol | 75 |
| Amino-acid | Na-L-Glutamate mono-hydrate | 20 |
|  | and Glycine | 160 |
| Polyamine | Spermidine tri-hydrochloride | 2.5 |
| | "invention 3" | |
| Buffer | Na$_2$HPO$_4$ di-hydrate | 1 |
| Sugar | D-Sorbitol | 75 |

TABLE 9-continued

Stabilisation of different viruses, and effect of polyamine
Stabiliser compositions used:

| Amino-acid | Na-L-Glutamate mono-hydrate | 20 |
|---|---|---|
| | and Glycine | 160 |
| Polyamine | none | 0 |

| | | Virus titre ($\log_{10}$ TCID$_{50}$/vial) | | |
|---|---|---|---|---|
| | | Wet titre before | Titre after freeze drying | |
| virus used and exp. code | Stabiliser | freeze-drying | Direct | 3 days 28° C. | 1 year + 4° C. |
| BRSV 04.20.001BD | no stab. | 5.8 | 4.6 | 3.5 | 2.8 |
| | Conv. stab | | 5.6 | 5.0 | 5.0 |
| | invention 1 | | 5.5 | 4.0 | 5.1 |
| | invention 3 | | 5.0 | 4.3 | n.a. |
| BRSV 04.20.001BF | no stab. | 6.2 | 3.6 | 3.6 | 2.6 |
| | Conv. stab | | 5.5 | 5.1 | 5.1 |
| | invention 1 | | 3.6 | 3.5 | 3.2 |
| | invention 2 | | 3.5 | 3.5 | 3.0 |
| | invention 3 | | 3.5 | 3.5 | n.a. |
| BRSV 04.20.001BL | no stab. | 5.8 | 4.6 | 4.2 | 3.4 |
| | Conv. stab | | 5.4 | 5.2 | 5.0 |
| | invention 1 | | n.a. | 5.2 | 5.0 |
| | invention 2 | | 5.4 | 5.4 | 5.0 |
| | invention 3 | | 5.3 | 5.0 | n.a. |
| EIV 03.20.003AA | no stab. | 9.3 | 7.2 | 6.5 | 6.6 |
| | Conv. stab | | 7.4 | 8.1 | 8.3 |
| | invention 1 | | 7.9 | 7.4 | 7.9 |
| | invention 3 | | 8.0 | 8.2 | n.a. |
| EIV 03.20.203S | no stab. | 9.1 | 6.9 | 5.6 | 4.3 |
| | Conv. stab | | 8.9 | 8.3 | 7.7 |
| | invention 1 | | 8.8 | 8.3 | 7.1 |
| | invention 3 | | 8.9 | 8.4 | n.a. |
| BCV 04.20.800AH | no stab. | 7.0 | 4.7 | <3.5 | 3.2 |
| | Conv. stab | | 6.1 | 5.8 | 5.5 |
| | invention 1 | | 5.7 | 4.0 | 4.2 |
| | invention 3 | | 5.6 | <3.5 | n.a. |
| BCV 04.20.800AN | no stab. | 6.6 | 5.9 | 4.4 | 3.9 |
| | Conv. stab | | 5.7 | 5.3 | 5.1 |
| | invention 1 | | 5.9 | 5.4 | 5.2 |
| | invention 2 | | 6.0 | 5.3 | 4.9 |
| | invention 3 | | 5.9 | 5.4 | n.a. |
| Myxoma 04.20.001R | invention 1 | 7.9 | 7.6 | n.a. | n.a. |
| | invention 3 | | 7.7 | | |
| PRV 04.20.004AB | no stab. | 9.1 | 7.3 | n.a. | n.a. |
| | Conv. stab | | 8.3 | | |
| | invention 1 | | 8.3 | | |
| | invention 3 | | 8.0 | | |
| PRV 03.20.003 G | Conv. stab | 9.0 | 8.0 | 7.9 | 7.9 |
| | invention 1 | | 8.1 | 7.9 | 7.9 |
| | invention 3 | | 7.8 | 7.4 | 8.0 |
| BHV 03AB | Conv. stab | 9.1 | 8.4 | 8.1 | 8.0 |
| | invention 1 | | 8.0 | 7.7 | 7.8 |
| | invention 3 | | 7.7 | 6.7 | n.a. |
| BHV 03AE | Conv. stab | 8.7 | 7.7 | n.a. | 7.5 |
| | invention 1 | | 8.5 | 8.2 | 8.4 |
| | invention 3 | | 8.3 | 8.1 | 8.2 |
| BHV 03 AN | Conv. stab | 8.6 | 8.4 | 8.1 | 8.1 |
| | invention 1 | | 8.2 | 8.1 | 8.1 |
| | invention 2 | | 8.4 | 8.5 | 8.3 |
| BHV 03 AO | no stab. | 8.8 | 7.6 | 7.9 | n.a. |
| | Conv. stab | | 8.3 | 8.1 | 8.0 |
| | invention 1 | | 8.0 | 8.2 | 8.0 |
| | invention 2 | | 7.9 | 8.2 | 7.9 |
| | invention 3 | | 7.5 | 7.9 | n.a. |
| BHV 03 AR | no stab. | 8.9 | 7.7 | n.a. | n.a. |
| | Conv. stab | | 8.1 | 8.2 | |
| | invention 1 | | 8.3 | 8.1 | |
| | Invention 2 | | 8.3 | 8.1 | |
| | invention 3 | | 8.1 | 7.5 | |

Comparative examples were performed with the prior art conventional stabiliser (Makoschey et al., supra), this is indicated as "Conv. stab".
n.a. = not available

TABLE 10

Stabilisation of different viruses, which were produced ACF
Stabiliser compositions used:
"invention 1", "invention 3", and conventional
stabiliser "Conv. stab" (see Table 9).

| | | Virus titre ($\log_{10}$ TCID$_{50}$/vial) | | | |
|---|---|---|---|---|---|
| ACF virus used and exp. code | Stabiliser | Wet titre before freeze-drying | Titre after freeze drying | | |
| | | | Direct | 3 days 28° C. | 1 year + 4° C. |
| PI3 03H | Conv. stab | 9.5 | 8.3 | 8.0 | 8.1 |
| | invention 1 | | 8.9 | 8.7 | 8.6 |
| | invention 3 | | 8.8 | 8.6 | 8.5 |
| BHV 03AD | Conv. stab | 8.8 | 8.3 | 7.9 | n.a. |
| | invention 1 | | 8.4 | 8.0 | |
| | invention 3 | | 8.0 | 7.8 | |
| PRV 03N | Conv. stab | 9.3 | 8.3 | 8.0 | 7.7 |
| | invention 1 | | 8.3 | 8.1 | 8.1 |
| | invention 3 | | 8.4 | 7.8 | 7.2 |
| PRV 03P | invention 1 | n.a. | 8.5 | 8.2 | n.a |
| | invention 3 | | 8.3 | 7.8 | |
| Myxoma 04.20.01L | Conv. stab | 7.4 | 7.2 | 7.4 | n.a |
| | invention 1 | | 7.2 | 7.2 | | n.a. = not available

TABLE 11

Replacement of glycine by compatible solute

Stabiliser compositions used:
"invention 3" and "Conv. stab" (see Table 9)
Modifications of invention 3:

| | Compound | g/l (4 × conc) |
|---|---|---|
| Buffer | Na$_2$HPO$_4$ di-hydrate | 1 |
| Sugar | D-Sorbitol | 75 |
| Amino-acid | Na-L-Glutamate mono-hydrate | 20 |
| | no Glycine | none |
| Compatible solute | Sarcosine | 80 or 160 |
| | or Betaine | 80 or 160 |
| | or Di-glycine | 80 or 160 |
| | or Choline | 80 or 160 |
| Polyamine | none | 0 |

| | | Virus titre ($\log_{10}$ TCID$_{50}$/vial) | | |
|---|---|---|---|---|
| virus used and exp. code | Stabiliser | Wet titre before freeze-drying | Titre after freeze drying | |
| | | | Direct | 3 days 28° C. |
| BHV 03AC | Conv. stab | 9.0 | 8.1 | 8.1 |
| | invention 3 | | 7.8 | 7.7 |
| | Invention 3 −/− glycine: | | | |
| | +Sarcosine 80 g/l | | 7.5 | 7.5 |
| | +Sarcosine 160 | | 8.1 | 7.6 |
| | +Betaine 80 | | 8.4 | 7.1 |
| | +Betaine 160 | | 8.1 | 7.1 |
| | +Di-glycine 80 | | 7.9 | 7.3 |
| | +Di-glycine 160 | | 8.0 | 7.7 |
| | +Choline 80 | | 7.9 | 6.9 |
| | +Choline 160 | | 7.5 | 5.7 |
| PRV 03M | Conv. stab | 9.0 | 8.1 | 7.6 |
| | invention 3 | | 7.6 | 7.0 |
| | Invention 3 −/− glycine: | | | |
| | +Sarcosine 80 g/l | | 7.8 | 7.4 |
| | +Sarcosine 160 | | 8.2 | 7.2 |
| | +Betaine 80 | | 7.2 | 6.8 |
| | +Betaine 160 | | 7.4 | 7.1 |
| | +Di-glycine 80 | | 7.6 | 7.4 |
| | +Di-glycine 160 | | 8.2 | 8.3 |

TABLE 11-continued

Replacement of glycine by compatible solute

| | | |
|---|---|---|
| +Choline 80 | 7.3 | 6.7 |
| +Choline 160 | 7.4 | 5.7 |

TABLE 12

Effect of buffer pH

Micro-organism used: BHV
Stabiliser composition used:
"invention 3" and "Conv. stab" (see Table 9)
Modifications of "invention 3" stabiliser

| | Compound | g/l (4 × conc) |
|---|---|---|
| Buffer | Na$_2$HPO$_4$ di-hydrate | 1 |
| | or Tris HCl-Citraat | 50 mM-10 mM |
| Sugar | D-Sorbitol | 75 |
| Amino-acid | Na-L-Glutamate mono-hydrate | 20 |
| | and Glycine | 160 |
| Polyamine | none | 0 |

Variations of pH are indicated in the table:

| virus used and exp. code | Stabiliser | Wet titre before freeze-drying | Titre after freeze drying Direct | Titre after freeze drying 3 days 28° C. |
|---|---|---|---|---|
| BHV 03U | Conv. stab, pH 7.1 | 8.8 | 8.0 | 7.8 |
| | Conv. stab, pH 7.4 | | 7.6 | 7.9 |
| | invention 3, pH 6.9 | | 7.9 | 7.3 |
| | invention 3, pH 7.4 | | 7.9 | 6.5 |
| | invention 3 –/– phosphate + Tris/Citraat, pH 6.9 | | 8.0 | 6.9 |
| | invention 3 –/– phosphate + Tris/Citraat, pH 7.4 | | 8.2 | 6.7 |

Virus titre (log$_{10}$ TCID$_{50}$/vial)

TABLE 13

Stabilisation of *E coli* bacteria
Micro-organism used: *E. coli* K12
Stabiliser composition used: "invention 1" (see Table 9). For comparison a standard bacterial stabiliser containing Albumin was used. This is indicated as "bac stab."

| Culture medium | Stabiliser | before freeze drying | direct after freeze drying |
|---|---|---|---|
| LB | bac stab | 3 × 10$^{10}$ | 6.5 × 10$^8$ |
| | invention 1 | | 2.4 × 10$^9$ |
| LB amp | bac stab | 3 × 10$^{10}$ | 3.5 × 10$^8$ |
| | invention 1 | | 2.4 × 10$^9$ |
| Blood agar | bac stab | 2.7 × 10$^{11}$ | 3.4 × 10$^9$ |
| | invention 1 | | 2.1 × 10$^{10}$ |

TABLE 14

Stabilisation of different bacteria
Micro-organism used: Different bacteria.
Stabiliser composition used: "invention 1" and "invention 3"
(see Table 9). For comparison a standard bacterial stabiliser containing Albumin was used. This is indicated as "bac stab."

| Bacterium, starting CFU/ml | Stabiliser | recovery % direct after freeze drying | recovery % after 3 days 28° C. | Cake quality |
|---|---|---|---|---|
| *E. coli* K12, 2.4 × 10$^9$ | none | 13 | 9 | – |
| | invention 1 | 33 | 1 | 0 |
| | invention 3 | 48 | 9 | 0 |
| *Salmonella gallinarum*, 4.0 × 10$^9$ | none | 24 | 16 | – |
| | invention 1 | 18 | 14 | + |
| | invention 3 | 34 | 17 | + |
| | bac stab | 100 | 57 | + |
| *Streptococcus equi*, 1.2 × 10$^9$ | none | 56 | 27 | 0 |
| | invention 1 | 60 | 6 | 0 |
| | invention 3 | 39 | 15 | + |
| | bac stab | 58 | 29 | + |
| *Staphylococcus carnosus*, 2.4 × 10$^9$ | none | 57 | 65 | 0 |
| | invention 1 | 64 | 67 | 0 |
| | invention 3 | 61 | 57 | 0 |

The invention claimed is:

1. A vaccine stabiliser composition consisting of at least one amino acid, at least one sugar, at least one polyamine, and water, wherein all compounds in the composition are chemically defined by consisting of identical molecules, and wherein the polyamine is at least one polyamine selected from the group consisting of ethylene-diamine, cadaverine, putrescine, spermidine and spermine;

wherein the at least one sugar is selected from the group consisting of glucose, lactose, sucrose, maltose, trehalose, sorbitol, mannitol, and a combination thereof; and wherein the at least one amino acid is selected from the group consisting of glutamate, glycine, or a combination thereof.

2. A vaccine stabilizer composition consisting of the composition according to claim 1 and a solute selected from the group consisting of sarcosine, betaine, Di-glycine, choline and a combination of two or more thereof.

3. The stabilizer composition according to claim 2, wherein the sugar is sorbitol, the at least one amino acid is a combination of amino acids that consists of glutamate and glycine, and the polyamine is spermine.

4. The stabilizer composition according to claim 2, wherein the sugar is sorbitol, the at least one amino acid is a combination of amino acids that consists of glutamate and glycine, and the polyamine is spermidine.

* * * * *

UNITED STATES PATENT AND TRADEMARK OFFICE
CERTIFICATE OF CORRECTION

| | | |
|---|---|---|
| PATENT NO. | : 8,778,868 B2 | Page 1 of 1 |
| APPLICATION NO. | : 11/908028 | |
| DATED | : July 15, 2014 | |
| INVENTOR(S) | : Van Gelder et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1457 days.

Signed and Sealed this
Eighth Day of March, 2016

Michelle K. Lee
*Director of the United States Patent and Trademark Office*